United States Patent [19]

Mateos et al.

[11] 3,996,132
[45] Dec. 7, 1976

[54] PURIFICATION OF UTERO-EVACUANT EXTRACTS FROM PLANT SUBSTANCES

[75] Inventors: Jose Luis Mateos; Luis Noriega, both of Mexico City, Mexico; Richard E. Huettemann, Hazlet; Ramesh Maganlal Kanojia, Somerville, both of N.J.

[73] Assignee: Ortho Pharmaceutical Corporation, Raritan, N.J.

[22] Filed: July 18, 1974

[21] Appl. No.: 489,688

[52] U.S. Cl. .................................. 210/31 C; 55/67
[51] Int. Cl.$^2$ ....................................... G01D 15/08
[58] Field of Search ..................... 210/31 C; 55/67; 424/195

[56] References Cited
OTHER PUBLICATIONS

B. J. Haywood, "Thin Layer Chromatography An Annotated Bibliography; 1964–1968.
Ann Arbor Science Pub. Inc., Ann Arbor, Mich., Abstract of Lundstrom et al., of J. Chromatog. 30, 271–272 (1967), p. 204.
Abstract of Eglington et al, Science 156, 1322–1335 (1967), p. 96.
Knapman et al., 1969 Edition, "Gas Chromatography Abstracts", The Institute of Petroleum, London, Eng. 1970 Abstract 10 of Ina et al, Tetrahedon Letters 1968 (23), 2777–2780, p. 2.
Introduction to Modern Liquid Chromatography by Synder and Kirkland. John Wiley and Sons, New York, N. Y. pp. 374–377. Received in Scientific Library June 23, 1974.

*Primary Examiner*—John Adee
*Attorney, Agent, or Firm*—Benjamin F. Lambert

[57] ABSTRACT

A method of purifying utero-evacuant extracts from the zoapatle plant is described. The method involves the purification of extracts from the zoapatle plant which contain an active principle utilizing chromatographic techniques.

16 Claims, No Drawings

0
PURIFICATION OF UTERO-EVACUANT EXTRACTS FROM PLANT SUBSTANCES

In co-pending application Ser. No. 460,258, filed Apr. 11, 1974 now abandoned, a method is described for obtaining utero-evacuant extracts from the zoapatle plant. The present invention relates to a method for purifying extracts from the zoapatle plant containing biologically active materials.

The zoapatle plant is a bush about 2 m. high that grows wild in Mexico. Botanically it is known as *Montanoa tomentosa* according to Gervantes, Fam. Compositae, Tribe Heliantheae; another variety of the species is *Montanoa floribunda*.

The plant has been used for centuries in the form of a "tea" or other crude aqueous preparations primarily as a labor inducer or menses inducer for humans. Its use has been documented in the literature, but definitive chemical and pharmacological studies have not been performed. The little work of a substantive nature that has been done is contradictory in its conclusions.

Natural plant substances are generally known to be exceedingly complex in their composition. Many compounds of similar chemical and physical properties, as well as those with strikingly dissimilar properties, are normally found in these substances and generally present a difficult separation and identification task. This has no doubt contributed in large measure to the conflicting reports seen in the literature.

A helpful and desirable tool in treating zoapatle for enhancement of the active principle would be a separation process which reduces the quantity of impurities without an attendant significant removal of the active material. Such a procedure should also have the attribute of simple, direct and economical operation if it is to be beneficial. The procedure should provide a method for rapidly producing an extract which would be the subject of further refined purification techniques but which itself has the biological activity above referred to and is itself useful biologically. It should also have the attributes of requiring a lower volume of material to be required by the patient.

In the current folk use of zoapatle, the user typically drinks a "tea" brewed from the leaves of the plant by boiling with water in the same manner used to prepare a hot beverage. She normally does this after having missed a menstrual period and thus is presumably pregnant, although it is known that many frankly pregnant women use the tea to terminate an unwanted pregnancy. The "tea" obviously contains a mixture of complex materials, some of which may be harmful to the user. In any case, the tea is bitter tasting and otherwise quite objectionable; since large amounts of the mixture are required, it represents an unpleasant form for use. Since such a complex mixture is present, many undesirable materials are ingested which are not necessary to produce the desired effect. The methods of the present invention, contrasted to the aqueous extraction method alone, remove a greater quantity of impurities while retaining biological activity thus reducing the variety of compounds and the volume of material that is required.

In the method described in co-pending application Ser. No. 460,258, aqueous extraction is used, but it is always preceded or followed by an organic extraction. For example, a portion of the plant preferably the leaves, containing the utero-evacuant materials is treated as follows:

a. aqueous extraction of the leaves of the plant followed by organic solvent extraction of the aqueous layer
 b. organic solvent extraction of the leaves of the plant followed by aqueous extraction of the organic layer.

Typically preferred solvents in this process are the water-immiscible aliphatic lower chain esters such as methyl acetate, ethyl acetate, butyl acetate and other longer chain esters, aliphatic hydrocarbons such as pentane, hexane and heptane, chlorinated hydrocarbons such as chloroform, carbon tetrachloride, and methylene chloride, aromatic hydrocarbons such as benzene, toluene, xylene and the like, and higher water-immiscible aliphatic alcohols such as butanol and pentanol. A suitable amount of zoapatle leaves, for example 3.5 kg., either dry or fresh, is washed with cold water and then extracted with water, preferably hot, or an organic solvent. The water extraction step is conveniently done at temperatures of from 25° C to 100° C and preferably at boiling for 10 minutes or more. The aqueous layer thus obtained is then separated from the plant residue giving a dark colored solution.

This solution is then extracted with an organic solvent. The organic extraction is conveniently performed at temperatures ranging from slightly above room temperature to the boiling point of the particular solvent. The organic extraction is continued until the desired amount of material is obtained, usually of the order of 1–2 hours. The organic extracts are then combined and evaporated to dryness.

As a result of the above extraction process, there is obtained a utero-evacuant extract greatly reduced in the amount of impurities when compared to the starting material.

The product obtained by the extraction process, although containing the active principle and possessing useful biological activity, still contains some undesirable materials which are not necessary to produce the desired effect.

The present invention provides a method of obtaining a biologically active material from the zoapatle plant whereby a purified material is obtained which is relatively free from undesirable materials but still retains the desired biological activity.

In the method of the present invention, suitable semipurified material, such as, for example, that obtained from the aqueous/organic solvent extract, is employed as the starting material. In one aspect of the present invention, the material to be purified is first dissolved in an organic solvent; the resulting solution is filtered and washed with an aqueous solution of a mild base, such as, for example, sodium bicarbonate, sodium carbonate, sodium acetate and the like to remove water-soluble and acidic impurities. It is preferred to use a saturated solution of the base. Suitable organic solvents include lower aliphatic ethers such as diethyl ether and dibutyl ether, lower aliphatic esters such as methyl acetate, ethyl acetate, butyl acetate and other long-chain esters, aliphatic hydrocarbons such as pentane, hexane and heptane, chlorinated hydrocarbons such as chloroform, carbon tetrachloride and methylene chloride, and aromatic hydrocarbons such as benzene and toluene, and the like. The solution may be concentrated and used directly in the next step, or the organic solvent may be removed by techniques known to those skilled in the art and the residue passed through a column of adsorbent material in an organic solvent. Suitable solvents include benzene and toluene, and the like. Adsorbent materials which may be employed include polymeric copolymeric materials such as vinyl acetate copolymer, various types of silica gel, and alumina. The preferred adsorbent is vinyl acetate copolymer. Several fractions are generally collected and the biologically active material in each of the fractions is followed by thin layer chromatography. The material thus obtained may be administered orally to women. However, where purer material is preferred, the fractions containing the active principle are combined and chromatographed over an adsorbent material such as silica gel, florisil or alumina. The column is eluted with an organic solvent or a mixture of solvents. Suitable solvents include aromatic hydrocarbons such as benzene, toluene, xylene and the like, and lower aliphatic esters such as methyl acetate, ethyl acetate, butyl acetate and the like, or mixtures of these solvents. Several fractions are collected and the active principle is again followed by thin layer chromatography. The fractions containing the desired material are combined and the solvent is removed. The material thus obtained is relatively pure and may be directly administered orally to women to induce labor or abortion or to induce a menstrual period. When further purification is desired, it can be achieved by additional column chromatography or preparative thin layer chromatography.

Alternatively, the semi-pure extract obtained from initial purification procedures can be further purified by chromatography over adsorbent materials such as, for example, silica gel and florisil utilizing a mixture of polar and non-polar solvents as the eluent. The preferred material is silica gel. Either neutral or acidic silica gel may be employed, but it is preferred to employ neutral silica gel. The material to be chromatographed is first dissolved in a suitable solvent, and the resulting solution is washed with mild alkali as described above. Any organic solvent which is immiscible with water and in which the material is soluble may be employed. Suitable solvents include ether, benzene, chloroform, carbon tetrachloride, methylene chloride, ethyl acetate, toluene and the like. The solvent, after drying over a suitable drying agent, is removed by techniques known in the art. The resulting residue is then added to a column of the adsorbent material packed in a suitable solvent and the column is eluted with a mixture of a polar and a non-polar solvent. Polar solvents which may be employed include alcohols such as ethanol, methanol, propanol, isopropanol and the like, ethyl acetate, butyl acetate and the like. Non-polar solvents include chlorinated hydrocarbons such as chloroform, methylene chloride and carbon tetrachloride, and hydrocarbon solvents such as pentane, hexane, heptane and the like. The preferred solvent mixture is isopropanol-chloroform. The fractions collected are evaporated to dryness at temperatures ranging from room temperature to about 40° C. The active principle in each of the fractions collected is monitored by thin layer chromatography or gas chromatography. The fractions containing the active principle are combined and can be further purified by preparative thin layer chromatography.

In another alternate procedure, the semi-pure starting material can be purified using high-pressure liquid chromatography. The starting material is first dissolved in a suitable organic solvent and the resulting solution is washed with mild alkali. The solvent is removed by techniques known to those skilled in the art and the residue is mixed with a small amount of packing material used in liquid chromatography. Packings such as the various types of silica gel, alumina and polyamide pellicle may be employed as the adsorbent. It is preferred to use silica gel as the packing. The mixture of residue and adsorbent are placed in a prep column containing additonal packing and the column is eluted with a non-polar solvent or a mixture of non-polar solvents such as dioxane, heptane, hexane, pentane and the like. The fractions collected are monitored by gas chromatography and/or thin layer chromatography. The fractions containing the active principle are then combined and the solvent removed. In carrying out the high-pressure liquid chromatography, generally a pressure of from about 300 to 500 psi can be employed. The preferred range is from 350 to 450 psi at room temperature.

As a result of the above purification methods, there is obtained a utero-evacuant material which is greatly reduced in the amount of impurities it contains when compared to the starting material. The purified form can be orally administered to women to induce labor or abortion or to induce a menstrual period. The material obtained herein has the unique ability of achieving the above results using usually only one oral dose containing about 40 mg. to about 100 mg. of material. In addition, these results are achieved with minimal side effects and in relatively short periods of time, usually of the order of 4–24 hours, depending upon the obstetrical condition of the patient.

EXAMPLE 1

The crude extract obtained from Preparation I (4.33 g.) is dissolved in ether (500 ml.) and the resulting solution is filtered and washed with saturated sodium bicarbonate solution (50 ml.). The ether is dried over anhydrous sodium sulfate, filtered and concentrated to dryness to afford a light yellow oil (3.4 g.). The yellow oil is then dissolved in benzene (50 ml.) and the solution added to a column (2 m × 10 cm) packed with 2 kgs. of OR-PVA Merck-O-gel* 2000. The column is eluted with benzene and the following fractions are collected after evaporation of the solvent.

* A vinyl acetate copolymer which swells in organic solvents, produced by E. M. Merck, Inc.

| Fraction | Volume (liters) | Residue (grams) |
| --- | --- | --- |
| 1 | 5.1 | 0.320 |
| 2 | 3.1 | 0.305 |
| 3 | 5.3 | 1.1 |
| 4 | 4.3 | 0.440 |

The material from fraction No. 3 (1.1 g.) is dissolved in benzene (10 ml.) and the solution is added to a dry silica gel column (60 g.) 1m × 2cm. The column is eluted with a mixture of benzene and ethyl acetate (4:1). After collecting 25 fractions of 125 ml. each, the eluent is changed to a 1:1 ratio of benzene ethyl acetate. The desired material is found in fractions 28–31 as determined by thin layer chromatography. The solvent is removed from fraction 28 and 0.046 g. of this material are administered orally to a woman 31 years old and 39 weeks pregnant. An observable physiological response began 13 minutes after administration and expulsion of the contents of the uterus occured 3 hours and 50 minutes after the material was given. Fractions 29–31 (0.350 g.) are dissolved in chloroform; the residue is applied to five preparative thin layer chromatography plates and the plates are developed 6 times with benzene and 3 times with benzene-ethyl acetate (4:1). The major band is separated and eluted with ethyl acetate. The solvent is removed to afford a residue having the following characteristics:

U.V. λ max.~230 nm (ε ≃ 2600). I.R. 2.91μ, 5.89μ, 5.95μ. Mass Spec. M+ 336, 334, 320, 318, 302; N.M.R. CDCl$_3$ 5.47, 5.29, 4.14, 4.11, 3.53, 3.15. TMS 1.75, 1.62, 1.14, 1.08 ppm.

The material thus obtained (0.054 g.) was administered to a woman who was 31 weeks pregnant. An observable physiological response began 15 minutes later and expulsion of the contents of the uterus occured 4 hours after initial administration.

EXAMPLE 2

The crude extract obtained from Preparation I (4.5 g.) is dissolved in ether (50 ml.) and the resulting solution is filtered and washed with a saturated solution of sodium bicarbonate (50 ml.). The ether solution is then dried over sodium sulfate and evaporated to dryness. The resulting residue (3.6 g.) is dissolved in chloroform (25 ml.) and added to a column (40 mm. inside diameter, 16 inches high) of neutral silica gel (200 g.) packed in chloroform. The column is eluted with chloroform, chloroform-isopropanol mixtures, and 25 ml. fractions are collected. Five such 25 ml. fractions are combined to give one 125 ml. fraction. About 75 such 125 ml. fractions are collected and evaporated to dryness in vacuo at a temperature below 40° C. The column is eluted as follows:

| Fractions (125 ml.) | |
|---|---|
| 1–18 | CHCl$_3$ |
| 19–30 | isopropanol:CHCl$_3$ (1:99) |
| 31–44 | isopropanol:CHCl$_3$ (1:49) |
| 45–51 | isopropanol:CHCl$_3$ (3:97) |
| 52–66 | isopropanol:CHCl$_3$ (1:24) |
| 67–75 | isopropanol:CHCl$_3$ (1:19) |

The fractions are monitored by thin layer chromatography as in Example 1 above. On the basis of thin layer chromatography, fractions Nos. 49–66 are combined and the solvent is removed to afford an oily residue (0.726 g.).

The residue is further purified by applying it to silica gel preparative thin layer chromatography plates. The plates are developed with isopropanol - chloroform (2:23) and the major band is eluted with MeOH—CHCl$_3$ (1:3) and evaporated to afford a residue of 540 mg. A 400 mg. portion of this material is chromatographed in a similar fashion to afford 268 mg. of an oil. The residue is characterized by U.V., I.R., Mass Spec. and N.M.R. and has characteristics similar to the material obtained in Example 1.

EXAMPLE 3

The crude extract (1 g.) from Preparation I is gently mixed with ether (5 ml.) in a 15 ml. test tube. The resulting solution is mixed with sodium bicarbonate (2 ml.) for one minute, the mixture centrifuged and the ether removed. The bicarbonate solution is washed with two additional 2 ml. portions of ether. The ether extracts are combined and the solvent is removed by evaporation. The dry residue is mixed with a small quantity of Pellosil*, and the mixture is inserted into the front end of a prep column (4 inches × ⅜ inch) containing Pellosil*. The packed column is installed into the instrument (du Pont 830 liquid chromatograph) and the column is eluted with a gradient from 2.5% dioxane in hexane to 7.5% dioxane in hexane at 400 psi. The column is eluted with 2.5% dioxane in hexane for 30 minutes, 5.0% dioxane in hexane for 30 minutes and 7.5% dioxane in hexane for 30 minutes. The collected fractions (the desired material is detected by U.V. chromophor measuring wavelength - 254 nm) are monitored by gas chromatography and thin layer chromatography. After collecting the 7.5% fraction for 10 minutes, the next 20 minute fraction Silica gel packing used for packings for liquid chromatography and manufactured by Reeve Angle & Co., Clifton, New Jersey. is collected and evaporated to dryness under nitrogen at 50° C. The residue from this fraction is characterized by U.V., N.M.R., I.R. and Mass Spec. and has characteristics similar to the material obtained in Example 1.

* A vinyl acetate copolymer which swells in organic solvents, produced by E. M. Merck, Inc.

PREPARATION OF STARTING MATERIAL

PREPARATION I

Water Extraction of Leaves Followed by Ethyl Acetate Extraction of the Aqueous Layer Two kg. of fresh zoapatle leaves are covered with H$_2$O (10 to 12 liters) and boiled for 1 hour. The mixture is then filtered through cheese cloth while hot and allowed to cool. The aqueous portion is then extracted twice with two volumes each of ethyl acetate. The ethyl acetate is then brought to dryness at 50° C in vacuo to afford 12 gm. of a dark green mass. The dark mass is treated with 500 ml. benzene and the mixture heated to boiling for about 15 minutes. The benzene layer is decanted and the residue washed with benzene until no further material is extracted. The benzene extracts are combined and reduced to dryness at 50° C under vacuum. A brownish mass results which is then successively extracted with separate portions of hexane in the same manner as described for the benzene treatment above until the hexane is colorless. The resulting residue, about 8 gm., has the consistency of thick syrup. This material is then dissolved in acetone (100 ml. or less) and 5 gm. of activated charcoal (Darco) is added thereto. The mixture is stirred at room temperature for 1 hour until the charcoal flocculates. The mixture is filtered and the filtrate evaporated to dryness under vacuum and slight heat (30° C) to afford 4 to 6 gm. of material which is very active as shown below.

500 mg. of the above material is administered orally to each of four non-pregnant human females on varying days of their menstrual cycle as indicated:

| Patient | Age | Weight | Day of Cycle | Bleeding |
|---|---|---|---|---|
| 1 | 25 | 40 kg. | 11 of 27–28 day cycle | within 2 hours of administration- natural period occurred on day 28. |
| 2 | 41 | 57 kg. | 24 of 25 day cycle | began spotting at 5 hours then regular period- natural period occurred on day 25. |
| 3 | 25 | 60 kg. | 15 of 28–29 day cycle | began spotting within 1 hour- natural period occurred on day 28. |
| 4 | 29 | 53.5 kg. | 22 of 28–30 day cycle | no bleeding until 27th day |

PREPARATION II

Organic Solvent Extraction of Leaves Followed by Aqueous Extraction of Organic Layer 2.0 kg. of dry zoapatle leaves are refluxed in $CHCl_3$ for 1 hour. After filtration, the chloroform extract is concentrated to dryness under reduced pressure and a temperature of 35°–50° C and yields 196 g. of a dark semisolid mass. This residue is extracted with hot ethanol-water (1:2). The aqueous ethanolic phase is re-extracted with $CHCl_3$; the $CHCl_3$ layer is separated and concentrated to dryness under reduced pressure affording a yellow-brown syrup. This is dissolved in ether and the solution washed with an aqueous saturated solution of sodium bicarbonate, 5% aqueous sodium hydroxide, water, and then dried over anhydrous sodium sulfate. Evaporation of the ether leaves a yellow oil (11.9 g.).

0.211 Gm. of this material was administered orally to a woman 11 weeks pregnant diagnosed as carrying a hidatiform mole. The patient was monitored for changes in arterial blood pressure, maternal heart rate and amniotic fluid pressure using the procedures described in the American Journal of Obstetrics and Gynecology, Vol. 96, No. 6, pages 849 to 856, Nov. 15, 1966, Noriega Guerra et al. Before administration of the medicament, amniotic fluid pressure (uterine contraction) was a normal 8 to 12 mm. of mercury without contraction. At about 19 minutes after administration of the medicament, the amniotic fluid pressure had increased to 25 mm. of mercury and significant uterine contractions began. There was no change in heart rate, and no change in arterial blood pressure. This continued for a period of 12 hours at which time the patient aborted. During this time there was no substantial deviation from the normal blood pressure and heart rate.

PREPARATION III

Water Extraction of Leaves Followed by Organic Solvent Extraction of Water Layer 634 g. of dry leaves are refluxed with 4.0 liters of water for 1 hour. The extract is decanted and extracted with chloroform. The chloroform phase is dried and filtered, and the solvent is evaporated under reduced pressure, leaving 4.55 g. of a semisolid mass. The aqueous phase is re-extracted with ethyl acetate. The organic phase is dried over anhydrous sodium sulfate, filtered, and concentrated under reduced pressure to yield 1.99 g. Both residues (from chloroform and from ethyl acetate) are combined.

What is claimed is:

1. The method of purifying extracts containing materials obtained from the zoapatle plant which comprises the steps of
    a. treating said extract with a water-immiscible organic solvent,
    b. treating the resulting solution with an aqueous solution of a mild base to remove water soluble and acidic impurities,
    c. passing the materials soluble in the organic phase at least once over a chromatography column of adsorbent material to separate from said phase said materials, and
    d. eluting the column with a second solvent or a mixture of solvents.
2. The method of claim 1 wherein the zoapatle plant is *Montanoa tomentosa* or *Montanoa floribunda*.
3. The method of claim 1 wherein the organic solvent comprises a lower aliphatic ester, an aliphatic hydrocarbon, an aromatic hydrocarbon, a chlorinated hydrocarbon or an aliphatic ether.
4. The method of claim 3 wherein the organic solvent is chloroform, carbon tetrachloride, methylene chloride or ether.
5. The method of claim 1 wherein the eluent is an aromatic hydrocarbon, a lower aliphatic ester, or a mixture of polar and non-polar solvents.
6. The method of claim 5 wherein the solvent is a mixture of benzene and ethyl acetate.
7. The method of claim 5 wherein the mixture of polar and non-polar solvents comprises isopropanol and chloroform.
8. The method of claim 1 wherein the adsorbent is vinyl acetate copolymer.
9. The method of claim 1 wherein the adsorbent is silica gel.
10. The method of purifying extracts containing materials obtained from the zoapatle plant which comprises the steps of
    a. treating said extract with a water-immiscible organic solvent,
    b. treating the resulting solution with an aqueous solution of a mild base to remove water soluble and acidic impurities, and
    c. passing the materials soluble in the organic phase through a high pressure liquid chromatograph column of adsorbent material and eluting the column with a second organic solvent or mixture of solvents at a pressure between 300 and 500 psi.
11. The method of claim 10 wherein the first organic solvent comprises a lower aliphatic ester, an aliphatic hydrocarbon, an aromatic hydrocarbon, an aliphatic ether or a chlorinated hydrocarbon.
12. The method of claim 10 wherein the second organic solvent comprises an aliphatic hydrocarbon or a mixture of hydrocarbons.
13. The method of claim 12 wherein the solvent is a mixture of hexane and dioxane.
14. The method of claim 10 wherein the pressure is between 350–450 psi.
15. The method of claim 10 wherein the adsorbent is silica gel.
16. The method of claim 10 wherein the zoapatle plant is *Montanoa tomentosa* or *Montanoa floribunda*.

* * * * *

UNITED STATES PATENT OFFICE
CERTIFICATE OF CORRECTION

Patent No. 3,996,132  Dated December 7, 1976

Inventor(s) Jose Luis Mateos et al.

It is certified that error appears in the above-identified patent and that said Letters Patent are hereby corrected as shown below:

In Column 5, lines 9-10, the word "N.M.R. $CDCl_3$ 5.47, 5.29, 4.14, 4.11, 3.53, 3.15. TMS 1.75, 1.62, 1.14, 1.08 ppm."
should read
--- N.M.R. $TMS^{CDCl_3}$ 5.47, 5.29, 4.14, 4.11, 3.53, 3.15, 1.75, 1.62, 1.14, 1.08 ppm ---.

In Column 5, line 15, the word "occured" should read --- occurred ---.

In Column 5, line 46, the word "(0.726 g.)" should read --- (0.725 g.) ---.

In Column 5, line 68, the word "(4 inches x 3/8 inch)" should read --- (4' x 3/8") ---.

UNITED STATES PATENT OFFICE
CERTIFICATE OF CORRECTION

Patent No. 3,996,132                    Dated December 7, 1976

Inventor(s) Jose Luis Mateos et al.

It is certified that error appears in the above-identified patent and that said Letters Patent are hereby corrected as shown below:

In Column 6, line 13, Lines 12 to end of Example 3 should read:

--- ...the next 20 minute fraction is collected and evaporated to dryness under nitrogen at 50°C. The residue from this fraction is characterized by U.V., N.M.R., I.R. and Mass Spec. and has characteristics similar to the material obtained in Example 1. ---.

The footnote begins with "Silica gel packing..." and is in the wrong place; it should be at the end of Example 3. Also, the asterisk to denote footnote is missing.

In Column 6, approximately Line 17, No need for second footnote beginning with "A vinyl acetate..."

Signed and Sealed this

Thirteenth Day of September 1977

[SEAL]

Attest:

RUTH C. MASON
Attesting Officer

LUTRELLE F. PARKER
Acting Commissioner of Patents and Trademarks